United States Patent [19]

Meier et al.

[11] 3,931,286

[45] Jan. 6, 1976

[54] NOVEL BENZOYLPHENYLACETIC ACID DERIVATIVES

[75] Inventors: Jean Meier, La Varenne Saint-Hilaire; Odile Le Martret, Paris, both of France

[73] Assignee: Roussel-UCLAF, Paris, France

[22] Filed: June 5, 1974

[21] Appl. No.: 476,667

[30] Foreign Application Priority Data
June 14, 1973 France .............................. 73.21622

[52] U.S. Cl.............. 260/469; 260/453 R; 424/298; 424/308
[51] Int. Cl.² ........................................ C07C 69/95
[58] Field of Search ...................... 260/469

[56] References Cited
UNITED STATES PATENTS
3,828,093  8/1974  Bays et al. .......................... 260/469

FOREIGN PATENTS OR APPLICATIONS
2,118,365  10/1971  Germany ........................... 260/469

Primary Examiner—Lorraine A. Weinberger
Assistant Examiner—Jane S. Myers
Attorney, Agent, or Firm—Hammond & Littell

[57] ABSTRACT

Novel benzoylphenylacetic acid derivatives of the formula

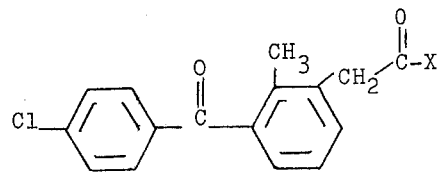

wherein X is selected from the group consisting of geranyloxy, pivaloyloxymethoxy and,

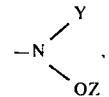

Z is alkyl of 1 to 4 carbon atoms and Y is selected from the group consisting of hydrogen and alkyl of 1 to 4 carbon atoms having anti-inflammatory and analgesic activity.

3 Claims, No Drawings

NOVEL BENZOYLPHENYLACETIC ACID DERIVATIVES

STATE OF THE ART

The literature describes certain derivatives of metabenzoylphenylacetic acids. French Pat. Nos. 1,516,775 and 1,546,478 and French Patent BSM 6444 M describe metabenzoylphenylacetic acids substituted or unsubstituted in one or the other aromatic ring or in the side chain. Belgian Pat. No. 718,466 describes the acids and derivatives of the carboxylic acid group such as alkyl esters, aryl esters, aminoalkyl esters, amides and hydroxamic acids. These references teach that the said compounds possess anti-inflammatory activity about equal to phenyl butazone and analgesic activity. In U.S. Pat. No. 3,741,988 is described the esterification of metabenzoylphenylacetic acids with polyhydroxy alcohols or their blocked derivatives. Glycerin esters or their blocked derivatives have been described for quinoleinic compounds in French Pat. No. 1,421,229 ($\alpha$-glycerin esters), in French Patent BSM 5310 M ($\beta$-glycerin esters) and in French Patent BSM 4775 M (blocked $\alpha$-glycerin esters in form of ketonides).

OBJECTS OF THE INVENTION

It is an object of the invention to provide the novel products of formula I.

It is another object of the invention to provide a novel process for the preparation of the products of formula I.

It is a further object of the invention to provide novel analgesic and anti-inflammatory compositions.

It is an additional object to provide a novel method of relieving pain and inflammation in warm-blooded animals.

These and other objects and advantages of the invention will become obvious from the following detailed description.

THE INVENTION

The novel benzoylphenylacetic acid derivatives of the invention have the formula

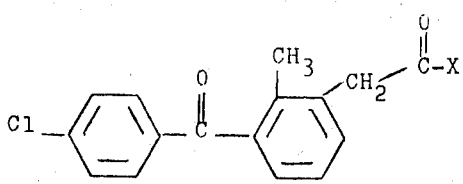

I wherein X is selected from the group consisting of geranyloxy, pivaloyloxymethoxy and

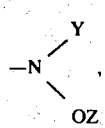

Z is alkyl of 1 to 4 carbon atoms and Y is selected from the group consisting of hydrogen and alkyl of 1 to 4 carbon atoms.

The novel process of the invention for the preparation of the compounds of formula I comprises subjecting a diazoketone of the formula

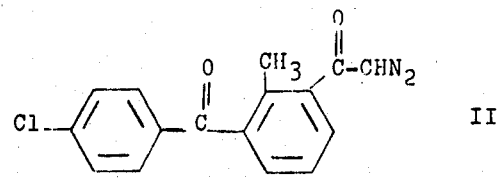

II either to a Wolff rearrangement in the presence of a silver salt and a compound of the formula

III to obtain the corresponding amide of formula I or to a Wolff rearrangement in the presence of a silver salt to form 2-methyl-3-(p-chlorobenzoyl)-phenylacetic acid which can be converted into its acid chloride and then reacted in one or the other of these two forms with a compound of formula III to obtain the corresponding amide of formula I. Also, a salt of 2-methyl-3-(p-chlorobenzoyl)-phenylacetic acid can be reacted with chloromethyl pivalate to obtain a compound of formula I where X is pivaloyloxymethoxy and the said acid or a functional derivative can be reacted with geraniol to obtain the compound of formula I where X is geranyloxy.

Preferably, when X is pivaloyloxymethoxy of the formula

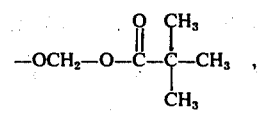

chloromethyl pivalate is reacted with an alkali metal salt of 2-methyl-3-(p-chlorobenzoyl)-phenylacetic acid such as its sodium or potassium salts. When X is geranyloxy, geraniol is reacted with 2-methyl-3-(p-chlorobenzoyl)-phenylacetic acid or its acid chloride, anhydride or mixed anhydride.

2-methyl-3-(p-chlorobenzoyl)-phenylacetic acid or its acid chloride may also be reacted with an hydroxylamine of formula III and if the acid is used, the reaction is preferably effected in the presence of a dehydrating agent such as dicyclohexyl carbodiimide. The diazoketone of formula II may be prepared by known methods.

The novel analgesic and anti-inflammatory compositions of the invention are comprised of an effective amount of at least one compound of formula I and a pharmaceutical carrier. The compositions may be in the form of injectable solutions or suspensions, tablets, capsules, gelules, drinkable solutions or emulsions, suppositories, pomades, creams or topical powders formed in the usual fashion.

The compositions are useful for the treatment of muscular, articulair or nervous pains, rheumatic affections, dental pains, zonas and migraines as an analgesic or for inflammatory conditions such as arthroses and lumbago and as a complementary treatment for infections and weak states.

The novel method of the invention for relieving pain and inflammation in warm-blooded animals comprises administering to warm-blooded animals an effective amount of at least one compound of formula I. The said compounds may be administered orally, parenterally or rectally or by topical application to the skin or mucous. The usual daily dose is 2 to 10 mg/kg depending on the treatment method and the compound.

In the following examples there are described several preferred embodiments to illustrate the invention. However, it is to be understood that the invention is not intended to be limited to the specific embodiments.

EXAMPLE 1

Pivaloyloxymethyl 2-methyl-3-(p-chlorobenzoyl)-phenylacetate STEP A: 2-methyl-3-(p-chlorobenzoyl)-phenylacetic acid A mixture of 5 g of 2-methyl-3-(p-chlorobenzoyl)-benzoic acid [prepared in French Pat. No. 2,085,638] and 50 ml of thionyl chloride was refluxed for 2 hours and excess thionyl chloride was distilled off under reduced pressure. The resulting acid chloride was dissolved in 50 ml of methylene chloride and 370 ml of a solution of diazomethane in methylene chloride were added progressively thereto at 0°C. After standing overnight at room temperature, the solvent was removed under reduced pressure and the obtained diazoketone was dissolved in 30 ml of dioxane. A mixture of 6 g of silver oxide, 14.5 g of sodium carbonate, 9.6 g of sodium thiosulfate and 70 ml of water was added progressively to the resulting solution at 70°C and after standing for 2 hours at 70°C, the mixture was filtered. The filtrate was acidified by addition of concentrated hydrochloric acid and the resulting precipitate was recovered, washed with water and crystallized from isopropyl ether to obtain 2-methyl-3-(p-chlorobenzoyl)-phenylacetic acid melting at 152°C.

STEP B: Pivaloyloxymethyl 2-methyl-3-(p-chlorobenzyl)-phenylacetate

A mixture of 3.37 g of the acid of Step A, 25 ml of hexamethylphosphortriamide and 0.57 g of a 50% suspension of sodium hydride in mineral oil stood until evolution of hydrogen ceased and then a solution of 1.78 g of chloromethyl pivalate in 10 ml of hexamethylphosphortriamide was progressively added thereto at room temperature. The mixture was stirred for 2 hours and was then poured into 250 ml of water. The mixture was extracted with isopropyl ether and the extracts were evaporated to dryness under reduced pressure. The residue was purified by chromatography over silica gel with a 95:5 mixture of methylene chloride-ethyl acetate as eluant. The fraction having Rf=0.65 was pivaloyloxymethyl 2-methyl-3-(p-chlorobenzoyl)-phenylacetate melting at 87°C.

EXAMPLE 2

Geranyl 2-methyl-3-(p-chlorobenzoyl)-phenylacetate STEP A: 2-methyl-3-(p-chlorobenzoyl)-phenylacetic acid chloride A solution of 5.8 g of 2-methyl-3-(p-chlorobenzoyl)-phenylacetic acid in 25 ml of thionyl chloride was refluxed for 1½ hours and excess thionyl chloride was removed to obtain 2-methyl-3-(p-chlorobenzoyl)-phenylacetic acid chloride melting at 62°–63°C.

STEP B: Geranyl 2-methyl-3-(p-chlorobenzoyl)-phenylacetate

A solution of 6.3 g of the acid chloride from Step A in 15 ml of benzene was added to a solution of 3.1 g of geraniol and 3 g of triethylamine in 15 ml of benzene while maintaining the temperature at about 25°C and the mixture was then stirred for 3 hours. The precipitate formed was removed by filtration and the filtrate was washed with water. The benzene was evaporated. The residue was chromatographed over silica gel with methylene chloride as eluant to obtain geranyl 2-methyl-3-(p-chlorobenzoyl)-phenylacetate with an Rf=0.42.

EXAMPLE 3

N-methoxy-2-methyl-3-(p-chlorobenzoyl)-phenylacetamide

Using the procedure of Step A of Example 1, 2-methyl-3-(p-chlorobenzoyl)-phenylacetic acid was reacted first with thionyl chloride and then diazomethane to obtain 2-methyl-3-diazoacetyl-4'-chlorobenzophenone which was purified over silica gel with methylene chloride as eluant. The product had an Rf=0.25 and melted at 95°C.

A mixture of 5 g of the diazoketone, 150 ml of dioxane, 5 ml of O-methylhydroxylamine and 10 ml of a 10% aqueous silver nitrate solution was heated for 1 hour at 60°C and then 200 ml of water were added. The mixture was cooled to 0°C and the precipitate was recovered, washed with water and dried. The product was crystallized from methanol to obtain N-methoxy 2-methyl-3-(p-chlorobenzoyl)-phenylacetamide melting at 150°C.

EXAMPLE 4

N-methoxy-N,2-dimethyl-3-(p-chlorobenzoyl)-phenylacetamide 1 ml of N,O-dimethylhydroxylamine was added progressively to a mixture of 2.88 g of 2-methyl-3-(p-chlorobenzoyl)-phenylacetic acid and 2.06 g of dicyclohexylcarbodiimide in 50 ml of chloroform and the mixture was stirred for 4 hours at room temperature. The precipitate was filtered off and the filtrate was evaporated to dryness to obtain N-methoxy-N,2-dimethyl-3-(p-chlorobenzoyl)-phenylacetamide.

EXAMPLE 5

Tablets were prepared containing 50 mg of the product of Example 3 and 350 mg of an excipient of lactose, amidon, talc and magnesium stearate.

PHARMACOLOGICAL STUDY

A. Anti-inflammatory Activity - Adjuvant Arthritis test

The injection of Freund type adjuvant into the rear paw of a rat provokes the appearance of a primary inflammatory lesion in the paw and then after a latency time of the order of 15 days, the release of a secondary arthritis affected the other rear paw as well as the front paws, the ears and the tail. On day zero of the test, the male rats received an injection in the rear paw of 0.1 ml of adjuvant (a suspension of dead mycobacterium bytiricum in mineral oil). The animals received orally from day zero to the 17th day the test product while the control anthritic animals did not receive the adjuvant and the normal control animals did not receive any treatment. On the 17th day, the increase in volume of the rear paws was compared to the normal controls. Also, the dosage of the $\alpha$ 2 M, glycoprotein absent in the normal rat but appearing notably in the inflammatory states, was determined. Also noted was the absence or presence of arthritic lesions in the tail, ears and front paws. The results were expressed by means of a conventional notation and addition of the resulting amounts gave the arthritic index.

The final results were determined by means of the $DA_{40}$ or the dose which reduced by 40% the arthritic index as compared to the arthritic controls. The $DA_{40}$ for the product of Examples 2 and 3 was 3 mg/kg.

B. Anti-inflammatory Activity - Naphthoylheparamine test

The test used the principle set forth by Jequier et al [Arch. Int. Pharmacodyn., Vol. 152 (1954), p. 15] and consisted of administering to rats weighing about 150 g a single injection of 1 mg of naphthoylheparamine into a rear paw to provoke formation of an inflammatory edema. The test products were orally administered 1 hour before the irritant injection. The volume of the paw was measured immediately before and 2 hours after the irritant injection and the increase in paw volume is a measure of the degree of inflammation. The $DA_{40}$ is the dose that diminished the inflammation by 40% compared to the controls. The $DA_{40}$ for the products of Examples 2 and 3 was 17 mg/kg and was 3.5 mg/kg for the product of Example 1.

C. Analgesic Effect

The test used was based on the fact noted by R. Koster et al [Fed. Proc., (1959), Vol. 18, page 412] wherein the intraperitoneal injection of acetic acid causes in mice characteristic repeated stretching and twisting movements which can persist for more than six hours. Analgesics prevent or suppress this syndrome which, therefore, can be considered as externalization of a diffuse abdominal pain.

A solution of 0.6% acetic acid in water containing 10% arabic gum was used and the dose which released the syndrome under these conditions was 0.01 cc/gm, that is 60 mg/kg of acetic acid. The test compounds were administered orally one-half hour before the intraperitoneal injection of acetic acid, the mice having fasted since the day before the experiment. For each dose and for each control, which are obligatory for each test, a group of 5 animals was used. For each mouse, the stretchings were observed and counted and then added for the group of 5 during a period of 15 minutes starting immediately after the injection of acetic acid.

The results were expressed by means of the $DA_{50}$ which is the dose reducing by 50% the number of stretching as compared to the controls. The products of Examples 2 and 3 had a $DA_{50}$ of 3 and 10 mg/kg, respectively.

Various modifications of the products and processes of the invention may be made without departing from the spirit or scope thereof and it should be understood that the invention is intended to be limited only as defined in the appended claims.

We claim:

1. A benzoylphenylacetic acid compound of the formula

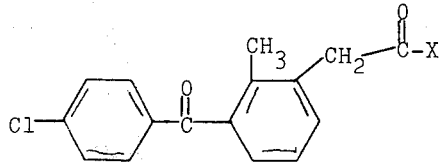

wherein X is selected from the group consisting of geranyloxy and pivaloyloxymethoxy.

2. A compound of claim 1 which is pivaloyloxymethyl 2-methyl-3-(p-chlorobenzoyl)-phenylacetate.

3. A compound of claim 1 which is geranyl 2-methyl-3-(p-chlorobenzoyl)-phenylacetate.

* * * * *